United States Patent
Mazzone et al.

(10) Patent No.: US 10,758,406 B2
(45) Date of Patent: Sep. 1, 2020

(54) HIGH EFFICIENCY HEAT EXCHANGE CATHETERS FOR CONTROL OF PATIENT BODY TEMPERATURE

(71) Applicant: ZOLL Circulation, Inc., San Jose, CA (US)

(72) Inventors: James D Mazzone, San Jose, CA (US); Masoumeh Mafi, Mountain View, CA (US)

(73) Assignee: Zoll Circulation, Inc., San Jose, CA (US)

( * ) Notice: Subject to any disclaimer, the term of this patent is extended or adjusted under 35 U.S.C. 154(b) by 567 days.

(21) Appl. No.: 15/395,923

(22) Filed: Dec. 30, 2016

(65) Prior Publication Data
US 2018/0185193 A1 Jul. 5, 2018

(51) Int. Cl.
*A61F 7/12* (2006.01)
*A61M 25/10* (2013.01)
*A61F 7/00* (2006.01)

(52) U.S. Cl.
CPC ............... *A61F 7/123* (2013.01); *A61F 7/12* (2013.01); *A61M 25/10* (2013.01); *A61F 2007/0054* (2013.01); *A61F 2007/0096* (2013.01); *A61F 2007/126* (2013.01); *A61M 2025/1086* (2013.01); *A61M 2206/10* (2013.01); *A61M 2230/50* (2013.01)

(58) Field of Classification Search
CPC combination set(s) only.
See application file for complete search history.

(56) References Cited

U.S. PATENT DOCUMENTS

| | | |
|---|---|---|
| 4,111,209 A | 9/1978 | Wolvek et al. |
| 4,259,276 A | 3/1981 | Rawlings |
| 4,298,006 A | 11/1981 | Parks |
| 4,911,232 A | 3/1990 | Colvin et al. |
| 5,837,003 A | 11/1998 | Ginsburg |
| 5,931,848 A | 8/1999 | Saadat |
| 6,019,783 A | 2/2000 | Philips et al. |
| 6,126,684 A | 10/2000 | Gobin et al. |
| 6,146,411 A | 11/2000 | Noda et al. |
| 6,149,677 A | 11/2000 | Dobak, III |
| 6,299,599 B1 | 10/2001 | Pham et al. |
| 6,301,904 B1 | 10/2001 | Goldstein |
| 6,338,727 B1 | 1/2002 | Noda et al. |
| 6,368,304 B1 | 4/2002 | Aliberto et al. |
| 6,451,045 B1 | 9/2002 | Walker et al. |
| 6,551,349 B2 | 4/2003 | Lasheras et al. |
| 6,554,797 B1 | 4/2003 | Worthen |
| 6,581,403 B2 | 6/2003 | Whitebrook |

(Continued)

FOREIGN PATENT DOCUMENTS

| | | |
|---|---|---|
| WO | WO99/52455 A1 | 10/1999 |
| WO | WO99/66970 A1 | 12/1999 |

(Continued)

OTHER PUBLICATIONS

PCT International Search Report dated May 15, 2018 in related PCT Application No. PCT/US2017/069098.

*Primary Examiner* — Joseph A Stoklosa
*Assistant Examiner* — Adam J Avigan
(74) *Attorney, Agent, or Firm* — Fish & Richardson P.C.

(57) ABSTRACT

Disclosure includes fluid-circulating heat exchange catheters, systems and related methods useable for controlling a patient's body temperature.

8 Claims, 6 Drawing Sheets

(56) References Cited

U.S. PATENT DOCUMENTS

| | | |
|---|---|---|
| 6,585,692 B1 | 7/2003 | Worthen |
| 6,589,271 B1 | 7/2003 | Tzeng et al. |
| 6,592,612 B1 | 7/2003 | Samson et al. |
| 6,610,083 B2 | 8/2003 | Keller et al. |
| 6,673,042 B1 | 1/2004 | Samson et al. |
| 6,679,907 B2 | 1/2004 | Dobak et al. |
| 6,695,873 B2 | 2/2004 | Dobak et al. |
| 6,702,840 B2 | 3/2004 | Keller et al. |
| 6,703,127 B2 | 3/2004 | Davis et al. |
| 6,706,060 B2 | 3/2004 | Tzeng et al. |
| 6,749,625 B2 | 6/2004 | Pompa et al. |
| 6,796,995 B2 | 9/2004 | Pham et al. |
| 6,835,334 B2 | 12/2004 | Davis et al. |
| 6,881,551 B2 | 4/2005 | Heller et al. |
| 7,255,709 B2 | 8/2007 | Walker et al. |
| 7,287,398 B2 | 10/2007 | Noda et al. |
| 7,389,653 B2 | 6/2008 | Kasza et al. |
| 7,566,341 B2 | 7/2009 | Keller et al. |
| 7,857,781 B2 | 12/2010 | Noda et al. |
| 7,963,986 B2 | 6/2011 | Machold et al. |
| 9,278,023 B2 | 3/2016 | Dabrowiak |
| 9,314,367 B2 | 4/2016 | Callister et al. |
| 9,492,633 B2 | 11/2016 | Dabrowiak |
| 2001/0007951 A1 | 7/2001 | Dobak, III |
| 2001/0016764 A1 | 8/2001 | Dobak |
| 2002/0045925 A1 | 4/2002 | Keller et al. |
| 2002/0116039 A1 | 8/2002 | Walker et al. |
| 2002/0151942 A1 | 10/2002 | Walker et al. |
| 2002/0183816 A1 | 12/2002 | Tzeng et al. |
| 2002/0193738 A1 | 12/2002 | Adzich et al. |
| 2003/0222378 A1 | 12/2003 | Xing et al. |
| 2004/0044387 A1 | 3/2004 | Pompa et al. |
| 2004/0050154 A1 | 3/2004 | Machold et al. |
| 2004/0076826 A1 | 4/2004 | Lee |
| 2004/0106969 A1 | 6/2004 | Dobak, III et al. |
| 2004/0111138 A1 | 6/2004 | Bleam et al. |
| 2005/0010272 A1 | 1/2005 | Pham et al. |
| 2005/0010273 A1 | 1/2005 | Walker et al. |
| 2005/0076924 A1* | 4/2005 | Dobak, III ............. A61B 18/02 128/898 |
| 2005/0187612 A1 | 8/2005 | Edwin |
| 2006/0161232 A1 | 7/2006 | Kasza et al. |
| 2007/0043409 A1 | 2/2007 | Brian, III et al. |
| 2007/0191810 A1 | 8/2007 | Kennedy |
| 2007/0207186 A1 | 9/2007 | Scanlon et al. |
| 2007/0250050 A1 | 10/2007 | LaFontaine |
| 2008/0071337 A1 | 3/2008 | Dobak, III et al. |
| 2008/0193653 A1 | 8/2008 | Oh |
| 2009/0043366 A1 | 2/2009 | Dae |
| 2009/0125087 A1 | 5/2009 | Becker et al. |
| 2009/0234325 A1 | 9/2009 | Rozenberg et al. |
| 2009/0247963 A1 | 10/2009 | Bleam et al. |
| 2009/0255276 A1 | 10/2009 | Kasza et al. |
| 2010/0036473 A1 | 2/2010 | Roth |
| 2010/0324635 A1 | 12/2010 | Kreck |
| 2011/0022136 A1 | 1/2011 | Scott et al. |
| 2011/0088413 A1 | 4/2011 | Lampe |
| 2011/0106051 A1 | 5/2011 | Saab |
| 2011/0152680 A1 | 6/2011 | Kim et al. |
| 2013/0079855 A1 | 3/2013 | Helkowski et al. |
| 2013/0090708 A1 | 4/2013 | Dabrowiak et al. |
| 2013/0178923 A1* | 7/2013 | Dabrowiak ............. A61F 7/12 607/105 |
| 2014/0094880 A1 | 4/2014 | Lim et al. |
| 2014/0114287 A1 | 4/2014 | Beasley et al. |
| 2015/0230975 A1 | 8/2015 | Dabrowiak et al. |

FOREIGN PATENT DOCUMENTS

| | | |
|---|---|---|
| WO | WO00/32126 A1 | 6/2000 |
| WO | WO2009/117586 A2 | 9/2009 |

* cited by examiner

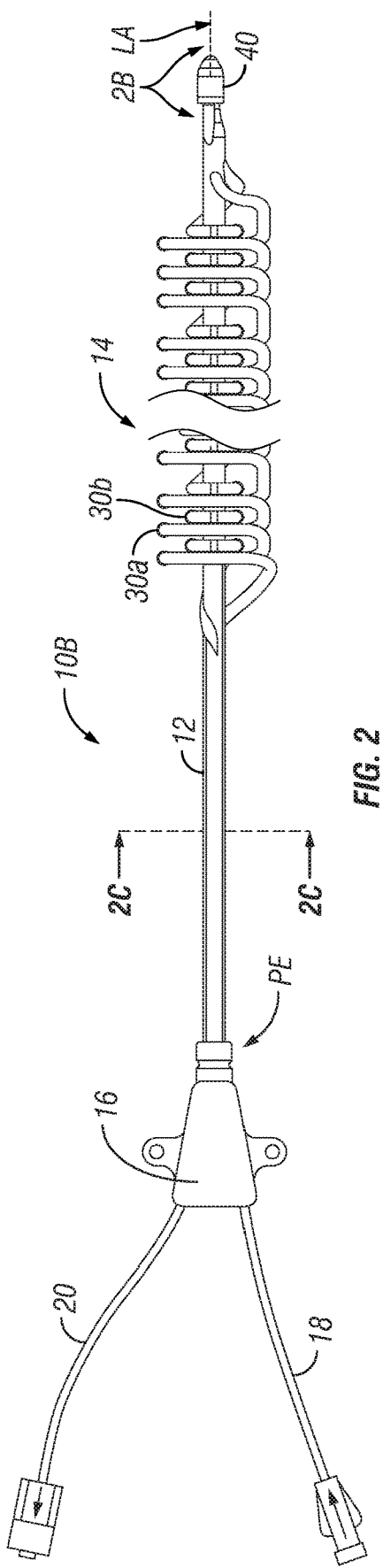
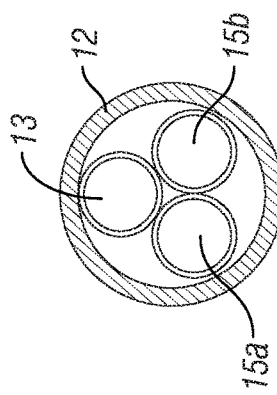
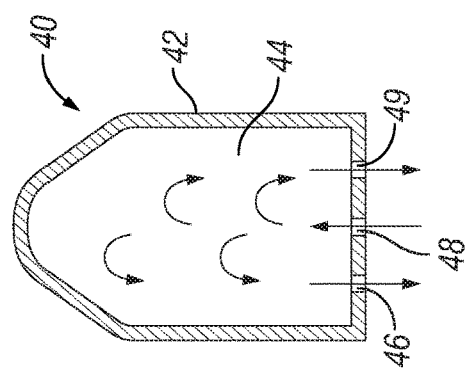
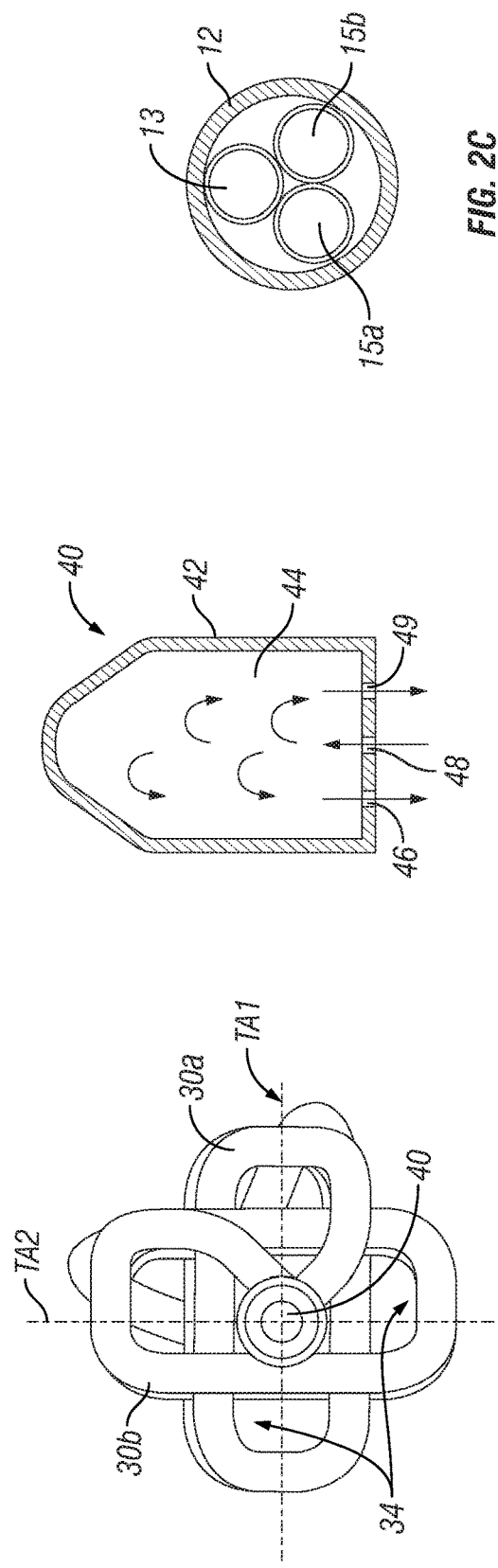

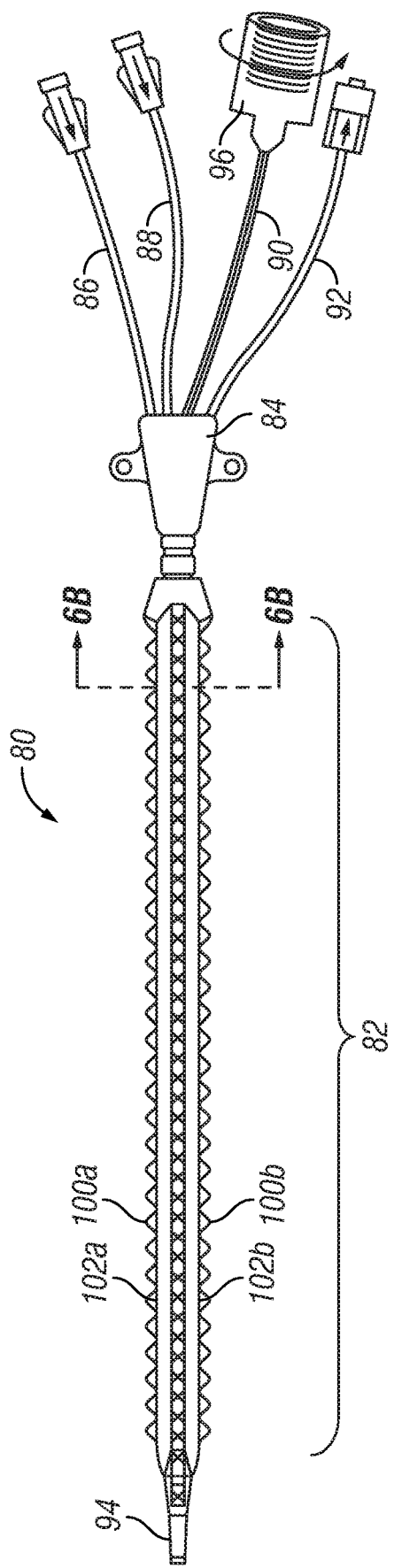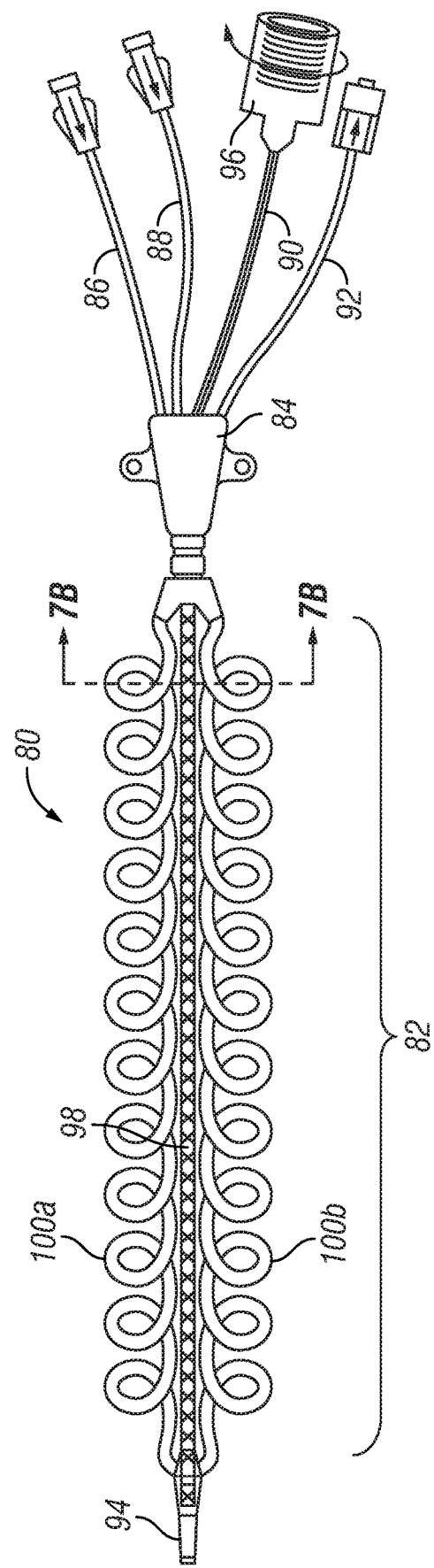

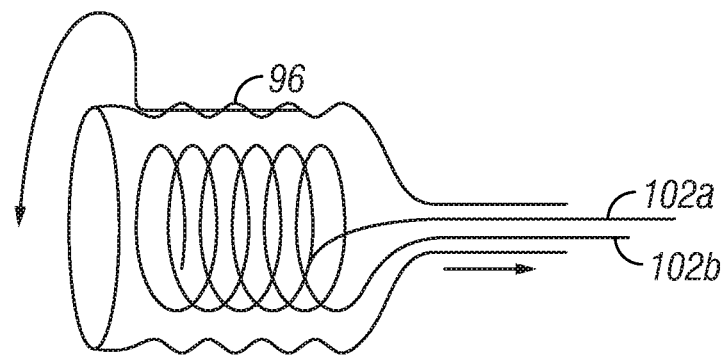 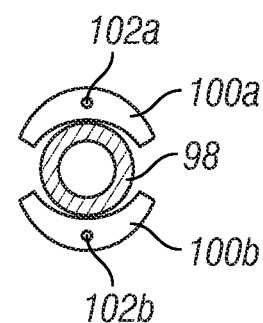
FIG. 6A  FIG. 6B
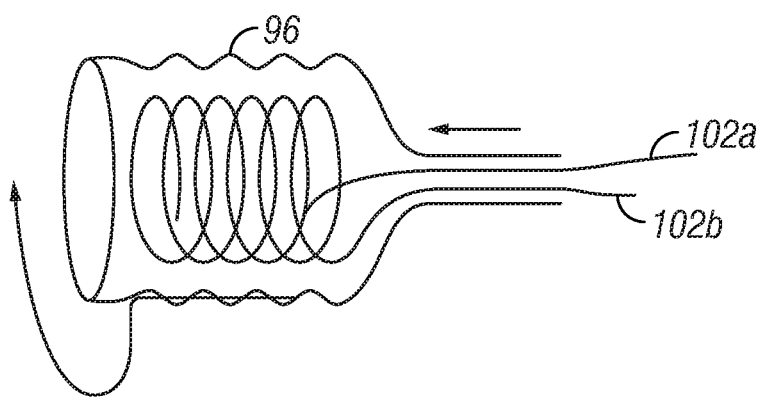 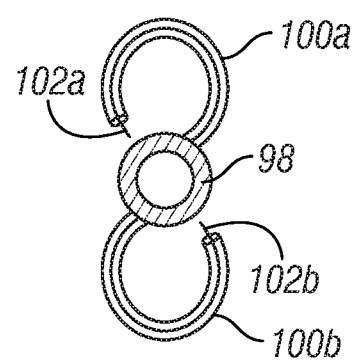
FIG. 7A  FIG. 7B

HIGH EFFICIENCY HEAT EXCHANGE CATHETERS FOR CONTROL OF PATIENT BODY TEMPERATURE

FIELD OF THE INVENTION

The present disclosure relates generally to the fields of medicine and biomedical engineering and more particularly to fluid-circulating catheters and related methods useable for controlling a patient's body temperature by endovascular heat exchange.

BACKGROUND

Pursuant to 37 CFR 1.71(e), this patent document contains material which is subject to copyright protection and the owner of this patent document reserves all copyright rights whatsoever.

In modern medicine there are numerous clinical situations in which it is desirable to control or modify body temperature of a patient. For example, hypothermia can be induced in humans and some animals for the purpose of protecting various organs and tissues against the effects of ischemic, anoxic or toxic insult. For example, hypothermia can have neuroprotective and/or cardioprotective effects in patients who suffer an ischemic event such as a myocardial infraction or acute coronary syndrome, post-anoxic coma following cardiopulmonary resuscitation, traumatic brain injury, stroke, subarachnoid hemorrhage, fever or neurological injury. Also, studies have shown that hypothermia can ameliorate nephrotoxic effects of radiographic contrast media (e.g., radiocontrast nephropathy) in patients who have pre-existing renal impairment.

One method for inducing hypothermia—or otherwise modifying or controlling a patient's body temperature—involves insertion of an endovascular heat exchange catheter into the patient's vasculature and circulation of a heat exchange fluid, such as warmed or cooled saline solution, through a heat exchanger located on the catheter. This results in exchange of heat between the circulating heat exchange fluid and blood that is coursing through the patient's vasculature. Because the blood circulates throughout the patient's entire body, this technique can be effective to change the patient's core body temperature to a desired target temperature and to thereafter maintain the target core body temperature for a period of time.

In some clinical situations, it is desirable to induce hypothermia as rapidly as possible. Once such example is in the treatment of acute myocardial infarction. Patients who are diagnosed with acute myocardial infarction are often treated with a coronary intervention or surgery (e.g., angioplasty or coronary artery bypass surgery) to reperfuse the ischemic myocardium. In at least one study, it was observed that patients with anterior wall infarctions whose core body temperature had been lowered to at least 35° C. prior to reperfusion by angioplasty had significantly smaller median infarct size than other patients with anterior wall infarctions whose core body temperature was greater than 35° C. at the time of reperfusion. This observation is not explained by other factors such as time-to-presentation, lesion location or quantity of antegrade coronary flow (TIMI Flow) prior to the angioplasty. This would suggest that, at least in acute myocardial infarction cases, it is desirable to lower the patient's body temperature to at least 35° C. as rapidly as practical so that reperfusion may also be accomplished as rapidly as practical after such hypothermia has been induced.

SUMMARY

In accordance with the present disclosure, there are provided catheter devices and systems useable for endovascular heat exchange and related methods for using such catheter devices and systems. The catheters, systems and methods described herein may provide high-efficiency heat exchange and the ability to rapidly raise or lower a patient's body temperature.

In accordance with one embodiment, there is provided a heat exchange catheter device which comprises an elongate catheter having a proximal end, a distal end, at least one inflow lumen, at least one outflow lumen and a longitudinal axis. At least first and second tubes having proximal and distal ends are coiled to form a series of elongated loops in each. Each such elongated loop has a length axis and a width axis. At least one elongated loop of the first tube extends around a section of the catheter such that the length axis of that elongated loop is substantially perpendicular or transverse to the longitudinal axis of the catheter. At least one elongated loop of the second tube also extends around the section of the catheter such that its length axis is also substantially perpendicular or transverse to the longitudinal axis of the catheter but nonparallel to the length axis of the elongated loop(s) of the first tube that also extend around the catheter. In at least some embodiments, the length axes of the first tube's elongated loops may be substantially perpendicular or transverse to the length axes of the second tube's elongated loops. In at least some embodiments the first tube's elongated loops may be aligned in a row with the second tube's elongated loops and/or the first tube's elongated loops may alternate with the second tube's elongated loops. The first and second tubes are connected to the inflow and outflow lumens such that heat exchange fluid will circulate in the inflow lumens, through the elongated loops and out of the outflow lumens. The elongated loops may be of any suitable elongate shape such as, for example, rectangular, rounded-corner rectangular, oval, ovoid or other oblong polygonal shapes. Catheters of this embodiment may be useable for controlling a subject's body temperature by a) inserting the catheter into the subject's vasculature and b) causing warmed or cooled heat exchange fluid to circulate through the elongated loops thereby resulting in exchange of heat between blood flowing through the subject's vasculature and the heat exchange fluid circulating through the elongated loops.

In accordance with another embodiment, there is provided a catheter device which comprises an elongate catheter having a heat exchange balloon attached thereto. Such heat exchange balloon comprises a central passageway and a plurality of heat exchange protuberances which extend outwardly from the central passageway. The catheter has at least an inflow lumen for circulation of fluid into the heat exchange balloon and an outflow lumen for circulation of heat exchange fluid out of the heat exchange balloon. The balloon may be a low pressure balloon formed of expandable material such as, for example, an expandable material selected from: Chloroprene, Latex, Silicone, Polyurethane (PU), Styrene Butadiene Styrene (SBS), and Styrene Isoprene Styrene (SIS). In at least some embodiments, the interior of the balloon may comprise separate flow paths for inflow and outflow of fluid. Such flow paths may include inflow and outflow channels within individual protuberances such that fluid will circulates into each protuberance through an inflow channel and out of each protuberance through an outflow channel. Catheters of this embodiment may be useable for controlling a subject's body temperature by a) inserting the catheter into the subject's vasculature and b) causing warmed or cooled heat exchange fluid to circulate through the heat exchange balloon, thereby causing the balloon to expand and resulting in exchange of heat between blood flowing through the subject's vasculature and the heat exchange fluid circulating through the heat exchange balloon.

Still further there is provided a catheter device which comprises an elongate catheter body having a proximal end, a distal end, an inflow lumen and an outflow lumen and a plurality of heat exchange tubes disposed in arcuate loops extending away from the catheter body. The inflow and outflow lumens are such that fluid will circulate from the inflow lumen, through the heat exchange tubes and then out of the outflow lumen. Catheters of this embodiment may be useable for controlling a subject's body temperature by a) inserting the catheter into the subject's vasculature and b) causing warmed or cooled heat exchange fluid to circulate in the inflow lumen, through the heat exchange tubes and out of the outflow lumen.

Still further there is provided a catheter device which has an elongate body with one or more tubular member(s) located on a distal portion of the elongate body. Such tubular member(s) may comprise heat exchange members through which heat exchange fluid may be circulated. The tubular member(s) are initially deployable in non-coiled configuration(s) and subsequently transitionable to coiled configuration(s). Advanceable coiling member(s) is/are used to facilitate such transition. The coiling member(s) may be formed of superelastic (e.g., nickel-titanium alloy, chromium cobalt) wire or any other suitable material or polymeric material that is pre-set or biased to assume a coiled configuration when relaxed but to become straight or substantially non-coiled when drawn taught. The coiling member(s) extend through or are affixed to exterior locations on the tubular member(s). The distal end(s) of the coiling member(s) is/are held at fixed locations on the elongate body of the catheter, distal to the tubular member(s). The proximal end(s) of the coiling member(s) is/are engaged with a coiling member advancement controller, such as a rotatable spooling device. The coiling member advancement controller is useable to initially draw the coiling member(s) to taught (preshaped), straight configuration(s), thereby causing the associate tubular members to assume non-coiled configurations. When the tubular members are in such non-coiled configuration(s) and not filled with fluid, they may be folded, furled, compressed, compacted, sleeved or otherwise disposed in low profile configurations suitable for initial insertion of the catheter device into a subject's body. Thereafter, the coiling member advancement controller is useable to advance the coiling member(s) distally, causing the coiling member(s) to slacken and assume their coiled configurations. The slackening and coiling of the coiling member(s) causes the tubular members to also assume corresponding coiled shapes. When in such coiled shapes, fluid (e.g., heat exchange fluid) may be circulated through the tubular member(s).

Still further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

FIG. 2 is a broken side view of the embodiment of FIG. 1.

FIG. 2A is a distal end view of the embodiment shown in FIG. 1 and FIG. 2.

FIG. 2B is a longitudinal sectional view through the distal tip member of the embodiment shown in FIGS. 1 and 2.

FIG. 2C is a cross sectional view through line 2C-2C of FIG. 2.

FIG. 6 is a side view of another embodiment of an endovascular heat exchange catheter having heat exchange members in non-coiled configurations.

FIG. 6A is an enlarged cut-away view of the coiling member advancement controller of the catheter of FIG. 6 rotated in a counterclockwise direction to cause the coiling members to retract proximally and be drawn to a taught, thereby causing the coiling members and the heat exchange members to be in non-coiled configurations.

FIG. 6B is a cross-sectional view through line 6B-6B of FIG. 6.

FIG. 7 is a side view of the heat exchange catheter of FIG. 6 with its heat exchange members in coiled configurations.

FIG. 7A is an enlarged cut-away view of the coiling member advancement controller of the catheter of FIG. 7 rotated in a clockwise direction to cause the coiling members to advance distally and slacken, thereby causing the coiling members and the heat exchange members to assume coiled configurations.

FIG. 7B is a cross-sectional view through line 7B-7B of FIG. 7.

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Figure 1:
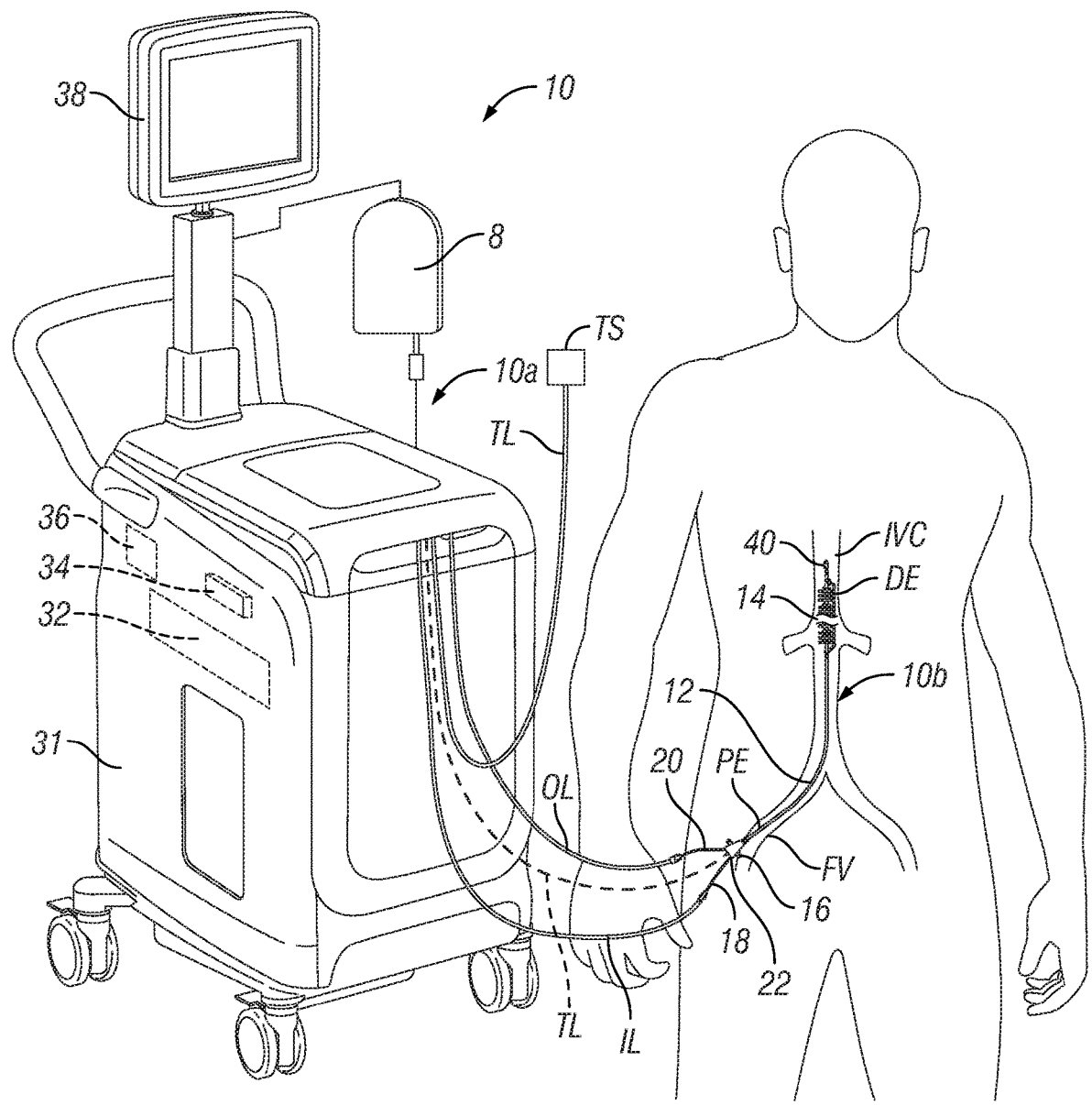
FIG. 1 shows an endovascular temperature management system which includes one embodiment of an endovascular heat exchange catheter.

FIG. 1 shows an endovascular temperature management system 10 which generally includes a control console 10a and an endovascular heat exchange catheter 10b. FIGS. 2 and 2A show further details of the embodiment of the endovascular heat exchange catheter 10b seen generally in FIG. 1.

The console 10a comprises a housing 31 within which, or on which, there are positioned heating/cooling apparatus 32 for alternately heating and cooling a heat exchange fluid, a pump 34 for pumping the heat exchange fluid and a programmable controller 36. A user interface 38, such as a liquid crystal display (LCD), is in communication with the controller 36. The user interface displays system information and also receives user input as well as sensor data, as described more fully herein.

A source of heat exchange fluid 8, such as a bag or container of sterile 0.9% NaCl solution, is connected by tubing to the heater/cooler 32. Also connected to the heater/cooler 32 are proximal ends of a heat exchange fluid outflow line OL and a heat exchange fluid inflow line IL.

At least one body temperature sensor TS is connected by way of a temperature lead TL, or alternatively by wireless connectivity, to the controller 36. This body temperature sensor TS may be positioned at any suitable location on or in the patient's body to monitor body temperature. In some embodiments, a plurality of temperature sensors TS may be employed. In some embodiments the temperature sensor TS may be positioned on or in the heat exchange catheter 10b or may be inserted through a lumen of the heat exchange catheter 10b as represented by dotted lines on FIG. 1. In other examples, the temperature sensor TS may be positioned elsewhere in or on the patient's body, such as on the patient's skin (e.g., axillary temperature sensor) or in the patient's vasculature, esophagus, rectum, bladder, ear canal or other suitable location.

In some embodiments, a temperature sensor TS may be inserted through a catheter and a second temperature sensor TS may be positioned at any other suitable location on or in the subject's body.

This embodiment of the endovascular heat exchange catheter 10b generally comprises a proximal catheter body 12 and an endovascular heat exchange assembly 14 attached to and/or extending distally from the proximal catheter body 12. In this particular embodiment, the proximal catheter body 12 has three lumens, an inflow lumen 15a, an outflow lumen 15b and an optional through lumen 13.

A hub 16 is mounted on the proximal end PE of the proximal catheter body 12. The hub 16 has an inflow connector 18 that is connected to the inflow lumen 15a of the catheter body 12 and an outflow connector 20 that is connected to the outflow lumen 15b of the proximal catheter body 12. Though not shown in the drawings, any catheter embodiment described herein may optionally include one or more additional lumens and such additional lumens may or may not be accessible by way of one or more additional connectors on the hub 16. Such optional additional lumens may extend through the entire length of the catheter or may terminate distally at an opening at the distal end DE of the heat exchange assembly 14 or may terminate at other opening(s) or ports(s) located at other location(s) on the catheter. Depending on their size, construction and opening/port location, any such optional lumen(s), when present, may be useable for passage of a guidewire or other device (e.g., temperature sensor, other type of sensor, etc.) and/or infusion or delivery of a substance (e.g., a medicament, fluid, radiographic contrast solution, etc.) or withdrawal of blood samples.

Figure 3:
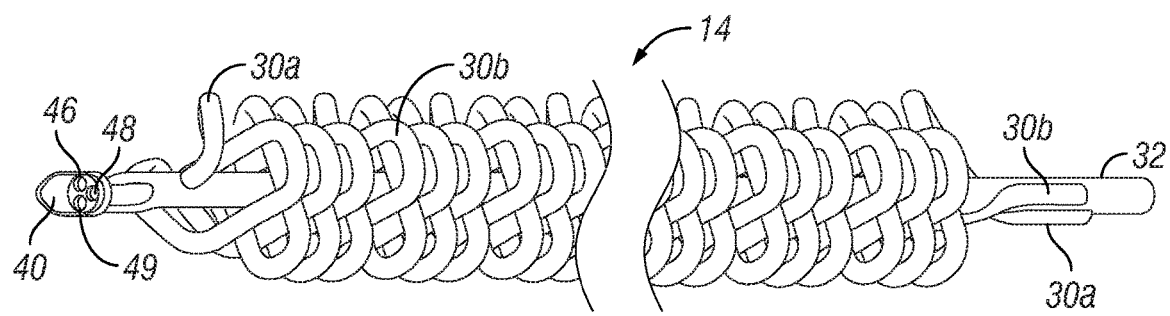
FIG. 3 is an enlarged, broken perspective view of the embodiment shown in FIGS. 1 and 2.

As may be fully appreciated from FIGS. 2 through 3, the heat exchange assembly 14 of catheter 10b comprises at least first and second coiled heat exchange tubes 30a, 30b.

In some embodiments, additional (e.g., third, fourth) heat exchange tubes may be used. The heat exchange tubes 30a, 30b may be formed of any suitable material. In the particular example shown in FIGS. 1 through 3, the heat exchange tubes may be advantageously formed of a noncompliant polymeric material, such as polyethylene terephthalate (PET), Pebax, Polyolefin, Polyurethane and/or Nylon, or other suitable compliant or noncompliant material. In some embodiments the heat exchange tubes 30a, 30b may expand and collapse depending on whether or not they are filled with fluid and, in such embodiments, the heat exchange tubes 30a, 30b may be referred to a "balloons." For some applications, the heat exchange tubes 30a and 30b may have outer diameters in the range of 2 mm-19 mm and wall thicknesses in the range of 0.0127 mm-0.1 mm.

In one example, the distal end of the first tube 30a is connected to the inflow lumen 15a at the distal end of the catheter body 12, and the distal end of the second tube 30b is connected to the inflow lumen 15a at the distal end of the catheter body 12. The first and second heat exchange tubes 30a and 30b are disposed on the catheter body 12 such that heat exchange fluid will flow in the distal direction through the inflow lumen 15a, which extends to the distal end of the catheter body 12, and then into the first and second heat exchange tubes 30a and 30b (either directly or via a recirculating tip), then in the proximal direction through the first and second heat exchange tubes 30a and 30b and then into the outflow lumen 15b of the catheter body 12.

In this non-limiting example, the recirculating distal tip member 40 comprises a generally bullet-shaped or blunt-tipped cylindrical structure which comprises a wall 42 which encloses an inner cavity 44. The distal end of inflow lumen 14 is connected to an inflow port 48 on the proximal portion of the recirculating tip member 40. In some embodiments, the catheter device 10b may include an optional through lumen that extends through the recirculating distal tip member 40 but is fluidly sealed from the inner cavity 44 such that fluid circulating through the inner cavity 44 will not leak into or enter the through lumen. One example of such a modified recirculating distal tip member having a through lumen is described in U.S. patent application Ser. No. 15/395,858 entitled Fluid-Circulating Catheters Useable For Endovascular Heat Exchange filed by Applicant on even date herewith, the entire disclosure of such copending application being expressly incorporated herein. Additionally incorporated herein by reference are the entire disclosure of U.S. Pat. No. 9,492,633 (Dabrowiak) and the entire disclosures of U.S. patent application Ser. No. 13/631,076 (US PG Pub. 2013/0178923) and Ser. No. 13/631,324 (US PG Pub. 2013/0090708).

The distal ends of the heat exchange tubes 30a, 30b are connected to outflow ports 46, 49 on the proximal portion of the distal tip member 40. Warmed or cooled heat exchange fluid will flow in the distal direction through inflow lumen 48 and into the inner chamber 44 of the recirculating tip member 40. Such warmed or cooled heat exchange fluid then exits though outflow ports 46, 49 and flows in the proximal direction through the coiled heat exchange tubes 30a, 30b where heat exchange occurs between the warmed or cooled heat exchange fluid and the patient's blood which flows in heat exchange proximity to the heat exchange tubes 30a, 30b. Causing the blood flow to be non-laminar or self-mixing can enhance the efficiency of the heat exchange. In this regard, the shape, spacing and arrangement of the elongate loops in heat exchange tubes 30a, 30b may be designed to increase blood contacting surface area on the tubes 30a, 30b and to disrupt laminarity of blood flow and improve the heat exchange, heating or cooling efficiency of the catheter 10b. For example, in the embodiment shown, the blood will flow not only around the heat exchange assembly 14 but will also course through blood flow channels 34 within the elongate loops of heat exchange tubes 30a, 30b, thereby enhancing the efficiency of heat exchange. However, at least in applications wherein the patient has not received anticoagulant medication, it may also be desirable for the shape, spacing and arrangement of the elongate loops in heat exchange tubes 30a, 30b to be designed so as to avoid creating so much turbulence or disruption of laminarity in the blood flow as to result in unwanted thrombogenesis.

After the heat exchange fluid has flowed in the proximal direction through the coiled heat exchange tubes 30a, 30b it will enter outflow lumen, 15b. Outflow lumen, 15b will extend within the proximal portion of the catheter body 12 or within the hub 16 such that all of the outflowing heat exchange fluid will pass through the outflow connector 20 and through outflow line OL back to the heater/cooler 32. It is to be appreciated that the inflow/outflow lumens 15a, 15b, the inflow/outflow connectors 18, 20 and the inflow/outflow lines IL, OL may be specifically sized to accommodate the volume and flow rate of fluid being channeled therethrough.

In operation of the system 10, the catheter 10b is inserted into the patient's vasculature such that the heat exchange assembly 14 is positioned within a blood vessel without fully blocking blood flow through that vessel. In the example of FIG. 1, the catheter is inserted through a femoral vein FV and advanced to a position where the entire heat exchange assembly 14 is in the inferior vena cava IVC. The temperature sensor(s) is/are positioned on or in the patient's body and connected to the controller 36. A user inputs a target body temperature to the controller 36 via the user interface 38. The controller then controls the pump 34 and/or heater/cooler 36 to circulate warmed or cooled heat exchange fluid through the catheter 10b, thereby causing the sensed patient body temperature to be adjusted to or maintained within a desired range of the input target body temperature for a desired period of time. In this manner the system 10 may be used to induce hypothermia, induce hyperthermia or attain normothermia.

In another example of a catheter 10b, the proximal end of the first tube 30a is connected to the inflow lumen 15a at the proximal end of the catheter body 12, and the proximal end of the second tube 30b is connected to the inflow lumen 15a at the proximal end of the catheter body 12. The first and second heat exchange tubes 30a and 30b are disposed on the catheter body 12 such that heat exchange fluid will flow in the distal direction through the inflow lumen 15a, and in the distal direction into and through the first and second heat exchange tubes 30a and 30b. The distal ends of the first and second heat exchange tubes 30a and 30b are coupled to the outflow lumen 15b at the distal end of the catheter body. The fluid flows from the first and second heat exchange tubes 30a and 30b into the outflow lumen 15b (either directly or via a recirculating tip), and through the outflow lumen 15b in the proximal direction.

In another example of a catheter 10b, the proximal end of the first tube 30a is connected to the inflow lumen 15a of the proximal catheter body 12. The proximal end of the second tube 30b is connected to the outflow lumen 15b of the catheter body 12. The distal ends of the first and second tubes 30a, 30b are coupled to each other by a connection piece or directly. These interconnected first and second heat exchange tubes 30a and 30b are disposed on the catheter body 12 such that heat exchange fluid will circulate from the inflow lumen of the catheter body 12, in the distal direction through the first heat exchange tube 30a, to the second heat exchange tube 30b (either directly or via a recirculating tip), then in the proximal direction through the second heat exchange tube 30b and into the outflow lumen 15b of the catheter body 12. In certain embodiments, the distal end of each heat exchange tube 30a, 30b may be connected to an inner cavity 44 of a recirculating tip member 40.

The system 10 may also be used with heat exchange catheters that incorporate heat exchange assemblies 14 that differ from the specific embodiment 14 used on the catheter 10b of FIGS. 1 through 3. For example, FIGS. 4 through 4C show another embodiment of a heat exchange assembly 14a and FIGS. 5 through 5B show another embodiment of a heat exchange assembly 14b.

Figure 4:
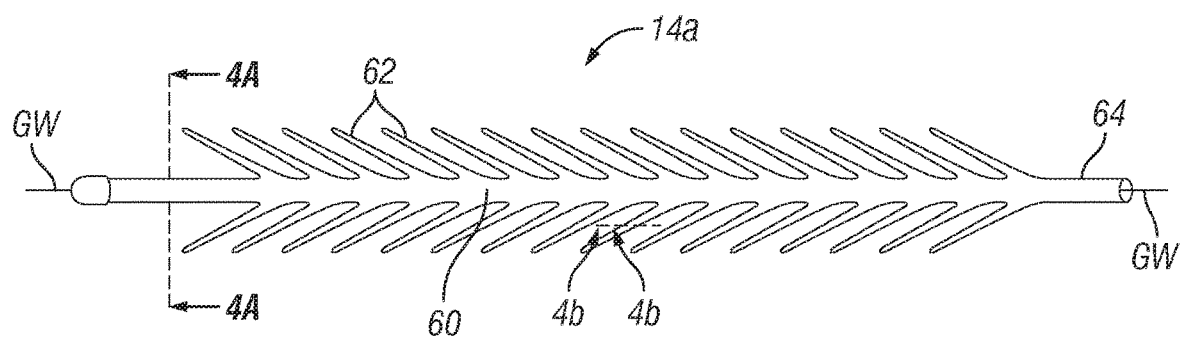
FIG. 4 is a side view of another embodiment of a endovascular heat exchange catheter.
Figure 4A:
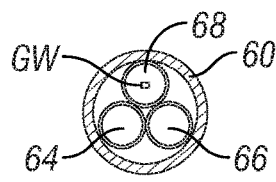
FIG. 4A is a cross sectional view through line 4A-4A of FIG. 4.
Figure 4B:
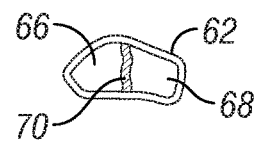
FIG. 4B is a cross sectional view through line 4B-4B of FIG. 4.
Figure 4C:
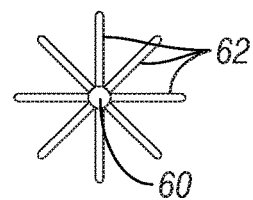
FIG. 4C is a cross sectional diagram showing a variant of the embodiment of FIG. 4 having heat exchange projections extending around the circumference of the catheter.

The heat exchange assembly 14a seen in FIGS. 4 through 4C comprises a low pressure/high surface area balloon having a central passageway 60 with heat exchange protrusions 62 extending outwardly from the central passageway 60. The protrusions 62 in FIG. 4 are shown extending toward the distal end of the catheter, in the typical direction of blood flow, however, in other embodiments the protrusions may extend in other directions relative to the catheter, e.g., perpendicular, or toward the proximal end of the catheter. This balloon may comprise a flexible molded part formed of an expandable material (e.g. Chloroprene, Latex, Silicone, Polyurethane (PU), Styrene Butadiene Styrene (SBS), and Styrene Isoprene Styrene (SIS), etc.) which allows a significant increase in the balloon surface area when the balloon is filled with heat exchange fluid. This will contribute to a higher heat transfer. Once the fluid is injected through the catheter shaft into the balloon, the finger-like protrusions on the balloon surface are inflated and thus create very high surface area for the heat transfer. The wall thickness of this balloon will also reduce as the balloon inflates, thereby improving efficiency of heat transfer. In some embodiments, the balloon may have a through lumen 68 that extends through the central shaft and useable for passage of a guidewire GW or for other purposes such as passage of a temperature sensor TS or other device, infusion of substances or withdrawal of blood samples. In some embodiments warmed or cooled heat exchange fluid may simply be circulated into an open inner cavity and the protrusions 62 of the balloon, e.g., through an inflow lumen 64, into the protrusions 62 and then into an outflow lumen 66. Optionally, the inflow lumen 62 and the outflow lumen 66 may be arranged concentrically, with the inflow lumen surrounding the outflow lumen or vice versa. In other embodiments, as seen in the sectional diagram of FIG. 4B, the inner cavity of the balloon may be portioned by walls 70 to define continuations of the inflow and outflow lumens 64, 66 thereby causing heat exchange fluid to circulate in specific flow paths or patterns within the balloon. Also, although the diagram of FIG. 4 shows only two rows of heat exchange protuberances 62 extending from opposite sides of the central passage 60, it is to be appreciated that such heat exchange protuberances 62 may be formed fully or partially around the circumference of the central passageway 60. For example, FIG. 4C shows a variant of this heat exchange assembly 14a wherein the balloon has heat exchange protuberances 62 which extend from locations all the way around the central passageway 60.

Figure 5:
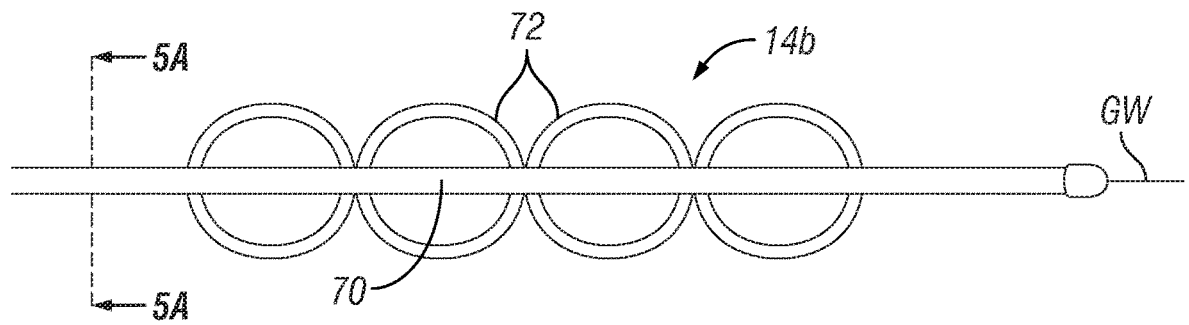
FIG. 5 is a side view of another embodiment of a endovascular heat exchange catheter.
Figure 5A:
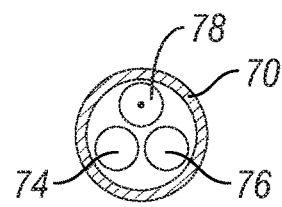
FIG. 5A is a cross sectional view through line 4A-4A of FIG. 4.
Figure 5B:
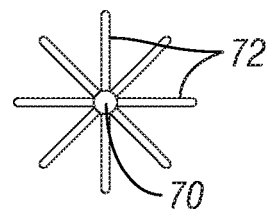
FIG. 5B is a cross sectional diagram showing a variant of the embodiment of FIG. 5 having arcuate heat exchange tubes extending around the circumference of the catheter.

FIGS. 5 through 5B show yet another embodiment of a heat exchange assembly 14b which comprises a catheter body 70 having an inflow lumen 74, an outflow lumen 76, an optional through lumen 78 through which a guidewire GW is shown to be inserted and arcuate heat exchange tubes 72. The arcuate heat exchange tubes 72 may be of the same size and material and the heat exchange tubes 30a, 30b of the first embodiment described above. As shown, the arcuate heat exchange tubes extend in arcuate loops outboard of or away from the catheter body 70. The inflow and outflow lumens 74, 76 may be arranged such that warmed or cooled heat exchange fluid flows distally through the inflow lumen 74 to a location distal to the heat exchange tubes 72 and then returns in the proximal direction through the heat exchange tubes 72 and then into the outflow lumen 76. Alternatively, the inflow and outflow lumens 74, 76 may be arranged such that warmed or cooled heat exchange fluid flows distally through the inflow lumen, and then into and distally through the heat exchange tubes 72 to a location distal to the heat exchange tubes 72 and then returns in the proximal direction through the outflow lumen 74. Although the diagram of FIG. 5 shows only two rows of arcuate heat exchange tubes 72 extending from opposite sides of the catheter body 70, it is to be appreciated that such arcuate heat exchange tubes 72 may be arranged fully or partially around the circumference of the central catheter body 70. For example, FIG. 5B shows a variant of this heat exchange assembly 14b wherein arcuate heat exchange tubes 72 are provided all the way around the central catheter body 70.

FIGS. 6 through 7B show a catheter device 80 having a distal portion 82, a proximal hub 84, an elongate body 98, and tubular members 100a, 100b positioned on the distal portion 82 of the elongate body 98. In the non-limiting example shown, the elongate body 98 comprises a braided tube having a lumen extending longitudinally therethrough. A connector 88 is connected to the proximal end of that tubular elongate body 98. The distal end of the elongate body 98 opens through an aperture in the distal tip member 94 of the catheter 80. Thus, the lumen of the elongate body 98 extends through the length of the catheter device 80 and may be used as a guidewire lumen, infusion lumen, medicament delivery lumen, temperature sensor lumen or as a utility lumen for various other purposes understood by those of skill in the art.

Coiling members 102a, 102b are embedded in the walls of tubular members 100a, 100b. The distal ends of the coiling members 102a, 102b are attached to the elongate body 98 and/or distal tip member 94. Proximal portions of the coiling members 102a, 102b extend through hub 84 and are windable onto and off of a spool within coiling member advancement controller 96. Each coiling member 102a, 102b is formed of superelastic (e.g., nickel-titanium alloy, chromium cobalt) wire or any other suitable material or polymeric material that is pre-set or biased to coiled configuration. The present coiled configurations of the coiling member(s) may be the same or different in size and/or shape. When the spool of the coiling member advancement controller 96 is rotated in a counterclockwise direction, the proximal portions of the coiling members 102a, 102b wind onto the spool, thereby drawing the coiling members 102a, 102b to taught non-coiled configurations and causing the tubular members 100a, 100b to also assume non-coiled configurations in which they may be folded, furled, compressed, compacted, sleeved or otherwise disposed in a low profile (e.g., reduced diameter) configuration as seen in FIGS. 6, 6A and 6B.

When the coiling member advancement controller 96 is rotated in the clockwise direction, proximal portions of the coiling members 102a, 102b will unwind from the spool and advance distally, thereby causing the coiling members 102a, 102b to slacken and assume their pre-set coiled configurations. This likewise causes the tubular members 100a, 100b to assume coiled configurations which correspond to the size(s) and shape(s) of the coils formed in the coiling members 102a, 102b as seen in FIGS. 7, 7A and 7B. With the tubular members 100a, 100b in such coiled configurations, heat exchange fluid may be circulated through the tubular members 100a, 100b to exchange heat with the subject's flowing blood. In alternative embodiments, the coiling member may be a nickel-titanium alloy wire or other material having a shape memory transition temperature of about 4-10 degrees C. or below 20 degrees or above 35 degrees, which transitions from a non-coiled to coiled configuration and vice versa. Transition from one configuration to the desired second configuration may be accomplished by changing the temperature of the coiling member to cause the coiling member to transition from a first configuration to a second configuration.

In the example shown, the distal tip 94 comprises a recirculating distal tip member which may be of the type described in U.S. patent application Ser. No. 15/395,858 entitled Fluid-Circulating Catheters Useable For Endovascular Heat Exchange filed on even date herewith, the entire disclosure of which is expressly incorporated herein by reference. Tubular member 100a is connected proximally to heat exchange fluid inflow connector 86 and distally to the recirculating distal tip member 94. Tubular member 100b is connected proximally to heat exchange fluid outflow connector 92 and distally to the recirculating distal tip member 94.

During typical operation, the catheter device 80 is inserted into the subject's vasculature while its tubular members 100a, 100b are in their collapsed, non-coiled configurations as shown in FIGS. 6, 6A and 6B. After the distal portion 82 has been advanced into the desired blood vessel (e.g., the inferior vena cava), the coiling member advancement controller 96 is rotated in the clockwise direction, causing the coiling members 102a, 102b and tubular members 100a, 100b to assume coiled configurations as seen in FIGS. 7, 7A and 7B. With the tubular members 100a, 100b in such coiled configurations, heat exchange fluid from inflow connector 86, through the first tubular member 100a in the distal direction, through the recirculating distal tip member 94, through the second tubular member 102b in the proximal direction and then out of outflow connector 92. In other embodiments, the tubular members 100a and 100b may be arranged such that fluid flows in the distal direction through both tubular members and flows in the proximal direction through an outflow lumen, or fluid may flow in a distal direction through an inflow lumen, and then in a proximal direction through the tubular members.

In many cases, the time required to raise or lower a patient's body temperature using an endovascular heat exchange catheter is dependent to at least some degree on the heat-exchanging efficiency of the heat exchange catheter. The catheters, systems and methods described herein may provide high-efficiency heat exchange and the ability to rapidly raise or lower a patient's body temperature.

Although the example of FIGS. 6 through 7B shows two tubular members 100a, 100b with two coiling members 102a, 102b, any suitable number of such tubular members and coiling members may be used and the relative number of tubular members 100a, 100b used for distally directed inflow and proximally directed outflow may vary.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A catheter device comprising:
    an elongate catheter having a proximal end, a distal end, at least one inflow lumen, at least one outflow lumen and a longitudinal axis;
    a first tube having a proximal end and a distal end, said first tube being coiled in a series of elongated loops each of which has a first length axis and a first width axis, the first length axis being longer than the first width axis;
    a second tube having a proximal end and a distal end, said second tube being coiled in a series of elongated loops each of which has a second length axis and a second width axis, the second length axis being longer than the second width axis;
    at least one elongated loop of the first tube being positioned to extend around a section of the catheter, the first length axis of the at least one elongated loop of the first tube being transverse to the longitudinal axis of the catheter; and
    at least one elongated loop of the second tube being positioned to extend around said section of the catheter, the second length axis of the at least one elongated loop of the second tube being transverse to the longitudinal axis of the catheter, wherein the second length axis of the at least one elongated loop of the second tube is substantially parallel to the first width axis of the at least one elongated loop of the first tube;
    wherein the first and second tubes are connected to the inflow and outflow lumens such that a fluid will circulate in the inflow lumen, through said first and second tubes and out of the outflow lumen.

2. A catheter device according to claim 1 wherein elongated loops have shapes selected from: rectangular, rounded-corner rectangular, oval, ovoid, triangle, and oblong polygonal.

3. A catheter device according to claim 1 wherein:
    a plurality of elongated loops of the first tube extend around said section of the catheter such that the length axis of each is substantially perpendicular to the longitudinal axis of the catheter; and
    a plurality of elongated loops of the second tube extend around said section of the catheter such that the length axis of each is substantially perpendicular to the longitudinal axis of the catheter and nonparallel to the length axes of the elongated loops of the first tube.

4. A catheter device according to claim 3 wherein said plurality of elongated loops of the first tube comprise all elongated loops of the first tube and said plurality of elongated loops of the second tube comprise all elongated loops of the second tube.

5. A catheter device according to claim 3 wherein the elongated loops are in a row wherein elongated loops of the first tube alternate with the elongated loops of the second tube.

6. A catheter device according to claim 1 wherein the length axis of said at least one elongated loop of the second tube is substantially perpendicular to the length axis of said at least one elongated loop of the first tube.

7. A catheter device according to claim 1 wherein the elongated loops are configured such that when the catheter device is inserted into the vasculature of a patient, the elongated loops will cause blood to flow in a non-laminar or self-mixing manner.

8. A catheter device according to claim 7 wherein the elongated loops are configured such that blood may flow through the elongate loops.

* * * * *